(12) United States Patent
Boppart et al.

(10) Patent No.: US 10,401,141 B2
(45) Date of Patent: Sep. 3, 2019

(54) METHOD AND APPARATUS FOR OBTAINING A THREE-DIMENSIONAL MAP OF TYMPANIC MEMBRANE THICKNESS

(71) Applicant: The Board of Trustees of the University of Illinois, Urbana, IL (US)

(72) Inventors: Stephen A. Boppart, Champaign, IL (US); Ryan L. Shelton, Champaign, IL (US); Paritosh Pande, Richland, WA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 93 days.

(21) Appl. No.: 15/811,999

(22) Filed: Nov. 14, 2017

(65) Prior Publication Data

US 2018/0156599 A1 Jun. 7, 2018

Related U.S. Application Data

(60) Provisional application No. 62/428,573, filed on Dec. 1, 2016.

(51) Int. Cl.
| | |
|---|---|
| *G01B 9/02* | (2006.01) |
| *A61B 1/227* | (2006.01) |
| *A61B 5/00* | (2006.01) |
| *A61K 9/00* | (2006.01) |
| *G01N 21/47* | (2006.01) |

(52) U.S. Cl.
CPC .......... *G01B 9/02091* (2013.01); *A61B 1/227* (2013.01); *A61B 5/0066* (2013.01); *A61K 9/0046* (2013.01); *G01B 9/02041* (2013.01); *A61B 5/7257* (2013.01); *G01N 21/4795* (2013.01)

(58) Field of Classification Search
CPC ............ G01B 9/02091; G01B 9/02041; A61B 1/227; A61B 5/0066; A61K 9/0046
See application file for complete search history.

(56) References Cited

U.S. PATENT DOCUMENTS

| | | | |
|---|---|---|---|
| 7,586,618 | B2 | 9/2009 | Marks et al. |
| 7,623,908 | B2 | 11/2009 | Boppart et al. |
| 7,725,169 | B2 | 5/2010 | Boppart et al. |

(Continued)

FOREIGN PATENT DOCUMENTS

WO  WO 02/088705 A2  11/2002

OTHER PUBLICATIONS

Ahmad et al, "Cross-correlation-based image acquisition technique for manually-scanned optical coherence tomography", 2009, Optics Express, vol. 17, No. 10, 12 pages (Year: 2009).*

(Continued)

*Primary Examiner* — David F Dunphy
(74) *Attorney, Agent, or Firm* — Sunstein Kann Murphy & Timbers LLP

(57) ABSTRACT

Methods and apparatus for combining a low coherence interferometry (LCI) technique for single-point thickness measurement with videoootoscopy for recording the image of a tissue such as the tympanic membrane (TM). TM thickness distribution maps are obtained by mapping the LCI imaging sites onto an anatomically accurate wide-field image of the TM, generated by mosaicking a sequence of multiple small field-of-view video-otoscopy images.

13 Claims, 8 Drawing Sheets
(7 of 8 Drawing Sheet(s) Filed in Color)

(56) References Cited

U.S. PATENT DOCUMENTS

| | | | |
|---|---|---|---|
| 7,787,129 | B2 | 8/2010 | Zysk et al. |
| 7,831,090 | B1* | 11/2010 | Krishnan ............ G06K 9/00214 345/419 |
| 8,115,934 | B2 | 2/2012 | Boppart et al. |
| 2003/0082104 | A1 | 5/2003 | Mertelmeier |
| 2003/0123713 | A1* | 7/2003 | Geng ................. G06K 9/00201 382/118 |
| 2004/0181128 | A1 | 9/2004 | Masters |
| 2006/0276709 | A1 | 12/2006 | Khamene et al. |
| 2009/0185191 | A1 | 7/2009 | Boppart et al. |
| 2010/0094137 | A1 | 4/2010 | Furlong et al. |
| 2013/0060131 | A1 | 3/2013 | Oghalai et al. |
| 2013/0222566 | A1* | 8/2013 | Murase ............. G01B 9/02076 348/78 |
| 2015/0351606 | A1 | 12/2015 | Ruppersberg et al. |
| 2015/0381968 | A1* | 12/2015 | Arora ...................... G06T 17/00 348/47 |
| 2016/0007840 | A1 | 1/2016 | Boppart et al. |
| 2016/0228208 | A1* | 8/2016 | Samsonov ............. A61B 90/39 |
| 2018/0055355 | A1* | 3/2018 | Sarunic ................ A61B 3/1233 |
| 2018/0325601 | A1* | 11/2018 | Mak ........................ G06T 15/00 |

OTHER PUBLICATIONS

Pitris et al, "High-Resolution Imaging of the Middle Ear With Optical Coherence Tomography", 2001, Biomedical Optics Express, vol. 127, 6 pages (Year: 2001).*

Nguyen et al, "Noninvasive in vivo optical detection of biofilm in the human middle ear", 2012, PNAS, vol. 109, No. 24, 6 pages (Year: 2012).*

Nguyen et al, "Non-invasive optical interferometry for the assessment of biofilnn growth in the middle ear", 2010, Biomedical Optics Express, vol. 1, No. 4, 13 pages (Year: 2010).*

Podleanu, "Optical coherence tomography", 2012, Journal of Microscopy, 11 pages (Year: 2012).*

American Academy of Family Physicians, "Otitis Media With Effusion," *Pediatrics*, vol. 113, No. 5, pp. 1412-1429 (May 2004).

Hall-Stoodley et al., "Direct Detection of Bacterial Biofilms on the Middle-Ear Mucosa of Children with Chronic Otitis Media," *JAMA*, vol. 296, No. 2, pp. 202-211 (Jul. 2006).

Jung et al., "Handheld Optical Coherence Tomography Scanner for Primary Care Diagnostics," *IEEE T. Bio-Med. Eng.*, vol. 58, No. 3, pp. 741-744 (Mar. 2011).

Marks et al., "Inverse scattering for frequency-scanned full-field optical coherence tomography," *J. Opt. Soc. Am. A*, vol. 24, No. 4, pp. 1034-1041 (Apr. 2007).

Nguyen et al., "Noninvasive in vivo optical detection of biofilm in the human middle ear," *Proc. Nat. Acad. Sci.*, vol. 109, No. 24, pp. 9529-9534 (Jun. 2012).

Pitris et al., "High-Resolution Imaging of the Middle Ear with Optical Coherence Tomography: A Feasibility Study," *Arch. Otolaryngol.*, vol. 127, pp. 637-642 (Jun. 2001).

Reed et al., "Gradient-index fiber-optic microprobes for minimally invasive in vivo low-coherence interferometry," *Opt. Lett.*, vol. 27, No. 20, pp. 1794-1796 (Oct. 2002).

Shelton et al., "Optical coherence tomography for advanced screening in the primary care office," *J. Biophotonics*, pp. 1-9, (Apr. 2013).

Takata et al., "Evidence Assessment of the Accuracy of Methods of Diagnosing Middle Ear Effusion in Children with Otitis Media with Effusion," *Pediatrics*, vol. 112, No. 6, pp. 1379-1387 (Dec. 2003).

Xi et al., "High-resolution three-dimensional imaging of biofilm development using optical coherence tomography," *J. Biomed. Opt.*, vol. 11, No. 3, pp. 134001-1-134001-6 (May/Jun. 2006).

Zysk et al., "Computational methods of analysis of human breast tumor tissue in optical coherence tomography images," *J. Biomed. Opt.*, vol. 11, No. 5, pp. 054015-1-054015-7 (Sep./Oct. 2006).

HEINE BETA® 200 Fiber Optic Otoscope, 1 page.

Welch Allyn Macro View™ sell sheet, 2 pages (2008).

Monroy et al., "Non-invasive Depth-Resolved Optical Measurements of the Tympanic Membrane and Middle Ear for Differentiating Otitis Media," *The Laryngoscope*, vol. 125, pp. E276-E282 (2015).

Szeliski, "Image alignment and stitching: A Tutorial," *Foundations and Trends in Computer Graphics and Vision*, vol. 2, pp. 1-104 (2006).

Bay, et al., "Speeded Up Robust Features, " *Computer Vision and Image Understanding*, vol. 110, pp. 346-359 (2008).

Pol et al., "Biomedical image mosaicking: A review," *In Communication and Computing Systems: Proc. Int. Conf on Comm. and Computing Systems (ICCS-2016)*, (Prasad et al., ed.), pp. 155-157 (2017).

Lowe, "Object recognition from local scale-invariant features," *Computer Vision*, pp. 1150-1157 (1999).

Can et al., "A feature-based, robust, hierarchical algorithm for registering pairs of images of the curved human retina," *Pattern Analysis and Machine Intelligence, IEEE Transactions on*, vol. 24, pp. 347-364 (2002).

Yang et al., "Covariance-driven mosaic formation from sparsely overlapping image sets with application to retinal image mosaicking," *Proceedings of the 2004 IEEE Computer Society Conference on Computer Vision and Pattern Recognition*, 6 pages, (2004).

Chanwimaluang et al., "Hybrid retinal image registration," *IEEE Trans. Inf. Tech. in Biomedicine*, vol. 10, pp. 129-142, (2006).

Jupeng et al., "A robust feature-based method for mosaic of the curved human color retinal images," *IEEE International Conf. on Biomedical Engineering and Informatics*, vol. 1, pp. 845-849, (2008).

Li et al., "Automatic montage of SD-OCT data sets," *Opt. Exp.*, vol. 19, pp. 239-248 (2011).

Van der Jeught et al., "Full-field thickness distribution of human tympanic membrane obtained with optical coherence tomography," *J. Association for Research in Otolaryngology*, vol. 14, pp. 483-494 (2013).

\* cited by examiner

METHOD AND APPARATUS FOR OBTAINING A THREE-DIMENSIONAL MAP OF TYMPANIC MEMBRANE THICKNESS

The present application claims priority of U.S. Provisional Patent Application Ser. No. 62/428,573, filed Dec. 1, 2016, and incorporated herein by reference.

This invention was made with government support under EB013723 awarded by the National Institutes of Health and CBET 14-45111 awarded by the National Science Foundation. The government has certain rights in the invention.

TECHNICAL FIELD

The present invention relates to apparatus and methods for acquiring a three-dimensional image of biological tissue, and, more particularly, to apparatus and methods for three-dimensional imaging of a tympanic membrane by combining visual imaging with low-coherence interferometry (LCI).

BACKGROUND ART

In various imaging applications, it is desirable to tessellate sub-images derived from a sequence of partial views in order to obtain a larger view than each sub-image can provide. In applications where two-dimensional image data are acquired via one imaging modality, and where depth information is obtained via a distinct imaging modality of comparable resolution to the first imaging modality, no one has ever considered the problem of how the spatially-resolved depth information of the distinct modalities could be combined to form an accurate three-dimensional representation. To address that problem, the present invention, as described below, is advanced.

Mosaicking techniques have been developed and applied in various contexts. Biomedical image mosaicking is reviewed in Pol et al., "*Biomedical image mosaicking: A review,*" in *Communication and Computing Systems: Proc. Int. Conf. on Comm. and Computing Systems (ICCS-2016)*, (Prasad et al., ed.), pp. 155-57 (2017), which is incorporated herein by reference.

Despite general agreement that the thickness of the human tympanic membrane (TM) varies considerably across different regions of the TM, very limited data on the TM thickness distribution are available in the literature, all derived from ex vivo specimens. Yet, TM thickness distribution is one of the key parameters in mathematical modeling of middle-ear dynamics. Such models play a fundamental role not only in advancing our understanding of the hearing process but also in designing ear prostheses. In the absence of adequate data on TM thickness distribution, most mathematical models tend to make overly simplified assumptions regarding the thickness of the TM; in some cases, to the extreme of assuming a single thickness value across the entire membrane.

TM thickness also provides valuable information about the state and functioning of the middle-ear, and is known to provide diagnostically useful information about several middle-ear pathologies. For example, it has been shown that the thickness of the TM in healthy human subjects is significantly different from the thickness in subjects with acute and chronic otitis media, as shown by Monroy et al., "*Non-invasive Depth-Resolved Optical Measurements of the Tympanic Membrane and Middle Ear for Differentiating Otitis Media,*" *The Laryngoscope*, vol. 125, pp. E276-82 (2015), which is incorporated herein by reference. A reliable method of determining in vivo TM thickness distributions could, therefore, also enable a more comprehensive diagnosis of various otologic diseases.

LCI is a well-known optical coherence technique capable of measuring one-dimensional depth-resolved tissue structure with a typical resolution of several microns. However, combining depth-profile information obtained at multiple points of an irregular (and, potentially, moving) surface into a consistent three-dimensional image presents a problem that requires solution.

Most image mosaicking techniques begin with an assumption of a suitable motion model describing the alignment between a pair of images. The motion model is characterized by a 2-D transformation matrix, which describes the coordinate transformation from one image to the next. Once the motion model is chosen, the parameters of the model are estimated by following either an intensity-based approach or a feature-based approach, taught by Szeliski, "*Image alignment and stitching: A tutorial,*" *Foundations and Trends in Computer Graphics and Vision*, vol. 2, pp. 1-104 (2006)v (hereinafter "Szeliski 2006"), which is incorporated herein by reference.

2006). In intensity-based methods, the model parameters are estimated by optimizing a suitable similarity metric representing the difference between pixel intensities of an image pair. Commonly used metrics include mean squared error, cross-correlation, or mutual information. Because the metric directly depends on pixel intensity values, these methods are sensitive to image deterioration resulting from various factors such as non-uniform illumination and defocus.

Feature-based techniques rely on matching landmark points between images. In these techniques, a set of matching image features such as edges, corners or other geometrical structures are first extracted from the images, and subsequently, the optimal image registration parameters are obtained by maximizing a similarity measure computed from the matched features. Some of the more popular feature matching methods include a Scale-Invariant Feature Transform (SIFT), as taught by Lowe, "*Object recognition from local scale-invariant features,*" *Computer Vision*, pp. 1150-57 (1999), and Speeded Up Robust Features (SURF), as taught by Surf, et al., "*Speeded Up Robust Features,*" *Computer Vision—ECCV* 2006, pp. 404-17 (2006), both of which publications are incorporated herein by reference. Unlike intensity-based methods, feature-based methods do not directly depend on the actual pixel values in an image, but rather on image features, which makes these methods more robust to variations in image quality. The performance of feature-based methods, however, largely depends on reliable detection of matched image features, which is challenging in cases when the images lack sharp distinctive features.

Several image registration techniques have been reported in the biomedical literature, mostly for retinal imaging, as listed here and as incorporated herein by reference.

Can et al., "*A feature-based, robust, hierarchical algorithm for registering pairs of images of the curved human retina,*" *Pattern Analysis and Machine Intelligence, IEEE Transactions on*, vol. 24, pp. 347-64 (2002);

Yang et al., "*Covariance-driven mosaic formation from sparsely overlapping image sets with application to retinal image mosaicking,*" *Proceedings of the* 2004 *IEEE Computer Society Conference on Computer Vision and Pattern Recognition*, (2004);

Chanwimaluang et al., "Hybrid retinal image registration," *IEEE Trans. Inf. Tech. in Biomedicine*, vol. 10, pp. 129-42, (2006);

Jupeng et al., "A robust feature-based method for mosaic of the curved human color retinal images," *IEEE International Conf on Biomedical Engineering and Informatics*, 2008, vol. 1, pp. 845-49, (2008); and Li et al., "Automatic montage of SD-OCT data sets," *Opt. Exp.*, vol. 19, pp. 239-48 (2011).

The foregoing techniques, however, are not directly applicable to TM image mosaicking for two main reasons. First, unlike retinal images, which have several distinctive features such as the bifurcations and crossovers of the blood vessels, TM images predominantly contain large homogeneous, nonvascularized regions lacking in sharp features. Second, due to the specular nature of TM, the spatial distribution of intensity, both within and between surface images of the TM, are widely heterogeneous depending on the angle and distance of the imaging probe.

Accordingly, novel mosaicking techniques are required, and those are described herein with reference to a device that may advantageously provide direct, accurate three-dimensional images of a tympanic membrane.

SUMMARY OF EMBODIMENTS OF THE INVENTION

In accordance with embodiments of the invention, methods and apparatus are provided for acquiring a three-dimensional mapping of a physical specimen characterized by a surface and a refractive index. The method has steps of:

obtaining a depth-resolved profile of the physical specimen at one or more fixed locations on each of the plurality of surface sub-images;

extracting at least one of an image feature for use as a landmark for local registration fo adjacent sub-images;

pairwise locally registering sub-images to define a set of transformation matrices, each transformation matrix characterizing a coordinate transformation between neighboring sub-images;

iteratively concatenating the transformation matrices so as to reference all of the transformation matrices to one of a plurality of coordinate frames of a plurality of sub-mosaics;

repeating the process of the steps of locally registering sub-images and iteratively concatenating the transformation matrices so as to reference all of the transformation matrices to a unitary global coordinate frame of the field of view of the surface of the physical specimen; and generating a three-dimensional globally co-registered mapping of the physical specimen based in part upon the depth-resolved profile at each of the plurality of locations.

In accordance with other embodiments of the present invention, additional steps may be included of correcting for error due to accumulation of mismatch errors in global registration of sub-mosaics, and/or interpolating sparsely-sampled areas in such a manner as to generate a smoothly colored map.

In accordance with further embodiments of the present invention, performing a depth scan at the specified point on the surface sub-image may include obtaining and processing a plurality of depth scans at the specified point. The method may also have further steps of blending edges between neighboring sub-images or interpolating between depths associated with successive spatial positions.

In accordance with yet further embodiments of the present invention, the method may account for increased optical depth due to the refractive index of the physical specimen. The depth scan may be obtained using low-coherence interferometry. The physical specimen may be a tympanic membrane of a subject in particular, and the method may, thus, also derive a measure of the tympanic membrane or of a biofilm disposed thereupon.

In accordance with another aspect of the present invention, a three-dimensional otoscopic mapping system is provided that has a hand-held probe with an otoscopic tip for insertion into an ear canal. The three-dimensional otoscopic mapping system has focusing optics for directing low-coherence light to ear tissue via the ear canal and for collecting scattered light within a field-of-view of a sub-image of the ear tissue, a dichroic beamsplitter for reflecting light scattered by a tympanic membrane of a subject onto a camera, and a low-coherence interferometer system for analyzing a depth profile at a plurality of points on the tympanic membrane. Finally, the system has a processor for mosaicking a plurality of the sub-images and the depth profile at each of the plurality of sub-images to form a map combining two-dimensional surface data with depth data in a visual representation.

In accordance with other embodiments of the present invention, the three-dimensional otoscopic mapping system may also have a steering mirror for scanning the field-of-view of the sub-image across the tympanic membrane, and the camera may include a detector array.

BRIEF DESCRIPTION OF THE DRAWINGS

The current patent or application file contains at least one drawing executed in color. Copies of this patent or patent application publication with color drawings will be provided by the Office upon request and payment of the necessary fee.

The foregoing features of the invention will be more readily understood by reference to the following detailed description, taken with reference to the accompanying drawings, in which:

FIG. 2A is an overview of the procedure, while FIG. 2B expands upon the steps of entailed in pairwise local registration.

FIGS. 3A-3C and 3D-3F, respectively, show validation results, for two subjects, of procedures described herein in accordance with an embodiment of the present invention. Panels 3A and 3D show the sequence of the small FOV images covering different regions of a TM, FIGS. 3B and 3E show mosaics generated from these images, and FIGS. 3C and 3F show TM images acquired using a commercial video-otoscope.

DETAILED DESCRIPTION OF EMBODIMENTS OF THE INVENTION

Definitions

Figure 1A:
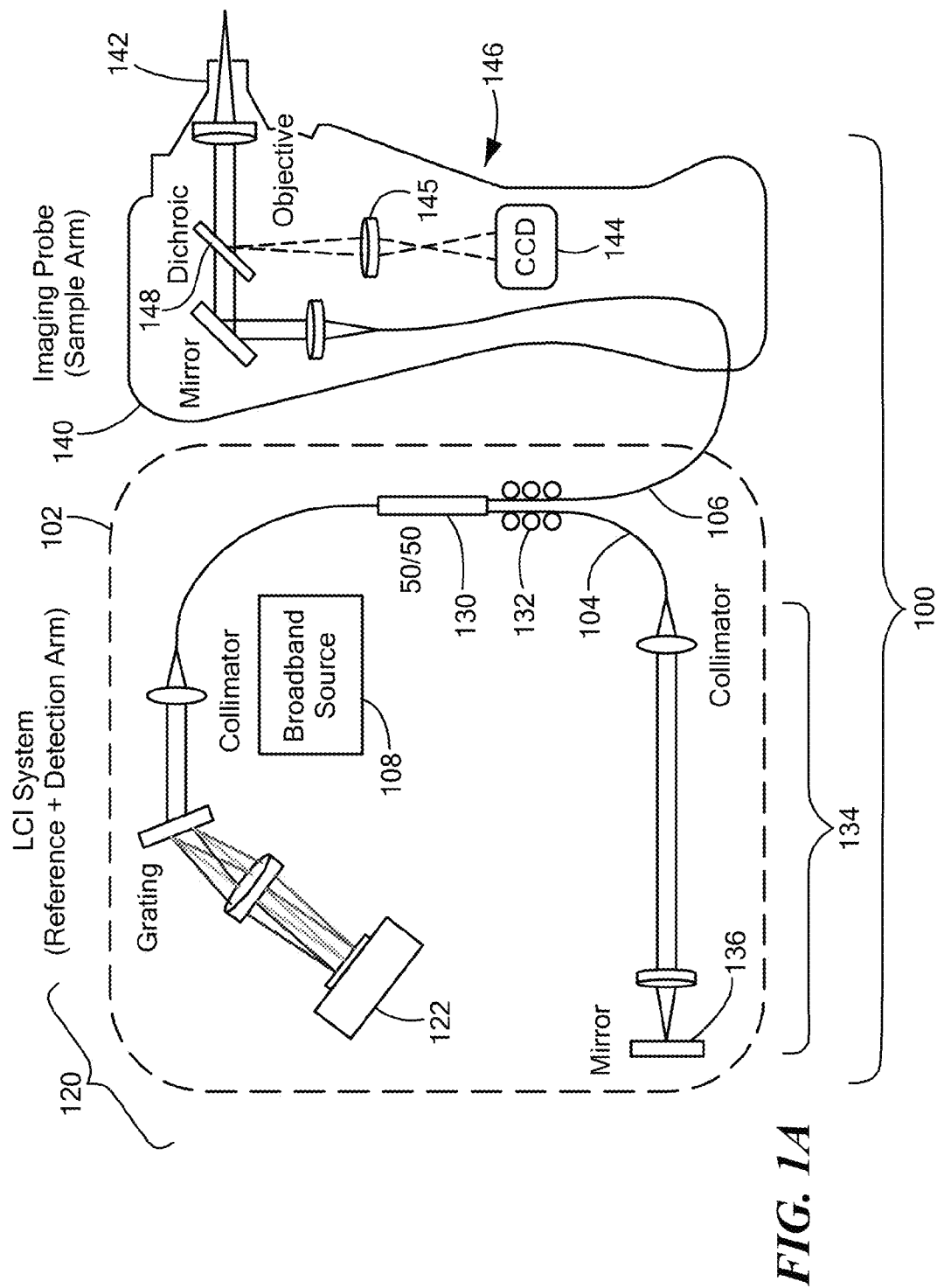
FIG. 1A shows component parts of a combined LCI-otoscope imaging system employed in accordance with an embodiment of the present invention.

The term "map" shall refer to any multidimensional representation, whether in tangible or otherwise perceptible form, or otherwise, whereby a value of some characteristic (amplitude, phase, etc.) is associated with each of a plurality of locations (or, vectors in a Euclidean space, typically $R^3$) corresponding to dimensional coordinates of an object in physical space, though not necessarily mapped one-to-one thereon. Thus, for example, the graphic display of the spatial distribution of some field, either scalar or vectorial, such as brightness or color, constitutes a map. Similarly, "mapping" refers to the rendering of a stated physical characteristic in terms of one or more maps.

A map may be referred to herein as an "image" if and only if the map associates a value with each location that is separately resolvable within the resolution capability of a specified imaging system.

The term "image," while generally referring to a mapping associating a scalar or vector with each resolvable point in the domain, shall include, without limitation, the following three distinct types of "image":

A mosaicked wide-field surface video image of the TM that is assembled from stitching together all the sub-images captured from the color CCD camera.

A 3-D image volume of the TM and any underlying biofilm or effusion based on sparsely sampled LCI axial depth scans collected from all the sampled points across the TM.

A color-coded "map" image of the TM surface that can be commonly superimposed over the grey-scale image of the first-listed image type. The color-scale used for this color image is based on the thickness of the TM/biofilm at each point, and if these points are widely spaced, then thickness values can be interpolated between the measured points.

"Smooth," as the term is used in the phrase "smoothly colored map," shall denote "continuous" (within the resolution of a specified digital representation) and need not require differentiability, infinite, or to any order. Thus, a map is "smoothly colored" if no discontinuity in color exceeds the increment constituting a single step of colorization.

The term "image feature" shall designate an identifiable region of one sub-image that extends to a neighboring sub-image and may thus serve in registration of the respective sub-images.

A "landmark," as the term is used herein, shall designate a point in a sub-image that may serve as a fiducial marker to establish correspondence between loci of the landmark in one or more spatially adjacent sub-images.

The terms "object," "sample," and "specimen" shall refer, interchangeably, to a tangible, non-transitory physical object capable of being rendered as an image.

When used to modify terms such as "beam," "pulse," etc., the terms "sample" and "signal" are used herein interchangeably.

The term "scattering medium," as used herein and in any appended claim, shall mean a medium in which an incident electromagnetic wave, of a wavelength range pertinent to the context under discussion, shall be characterized by a mean free path to scatter that is substantially shorter than the dimension of the medium in the propagation direction of the incident electromagnetic wave.

The term "scattering biological tissue," as used herein and in any appended claim, shall mean an organized ensemble of interconnected cells of an organism that has the optical properties associated with a scattering medium, as defined above.

The term "low-coherence" (or "broadband," as used interchangeably herein) applies to a source of illumination for which the coherence length is shorter than 30 µm, and/or for which $\Delta k/k_0$ is at least 10%, with $k_0$ denoting the central wavenumber of the spectrum illuminating the sample, while $\Delta k$ denotes the range of illuminating wavenumbers. It is to be understood that, within the scope of the present invention, the wavelength of the source need not be fixed in time, indeed, the wavelength of the source may be swept in time.

A "depth-resolved profile" shall include profiles based on optical scattering and refractive index variations over depth.

A "local registration" shall designate the registration of a sub-image relative to one or more nearest neighbor sub-images.

To address the challenges of TM image mosaicking discussed above, a novel two-step mosaicking method is now described, wherein, in accordance with embodiments of the present invention, a coarse image registration based on the correlation of gross image features is followed by a finer intensity-based co-registration process.

For heuristic convenience, embodiments of the present invention are described in terms of imaging the human tympanic membrane, since, as discussed in the Background Section, it is with respect to this application that the inventive techniques described herein are particularly suited and demonstrated for the first time. However, it is to be understood that the present invention, as claimed below, may be beneficial in other applications, and that all such applications are intended to be within the scope of the claimed invention.

In accordance with embodiments of the present invention, methods and apparatus are provided for obtaining thickness distribution for the in vivo human TM by using data acquired from a combined LCI-otoscope system, designated generally by numeral 100, and described with reference to FIG. 1A. The combined LCI-otoscope system 100 may also be referred to herein as a "hand-held imaging system."

TM thickness maps are obtained by mapping the LCI imaging sites onto an anatomically accurate wide-field image of the TM generated by mosaicking the sequence of multiple small field-of-view video-otoscopy images of the TM. Descriptive statistics of the thickness measurements obtained from different regions of the TM may also be derived.

Data are acquired from hand-held imaging system 100 in such a way as to combine LCI for single-point thickness measurements with video imaging for recording the surface images of the TM as the imaging probe is moved and directed across different parts of the membrane. The approach described herein may advantageously provide useful information for advancing a fundamental understanding of the functioning of the middle ear, through experiments and modeling, and may also advantageously provide significant diagnostic information in the form of normative TM thickness distribution maps, much like the retinal thickness maps that are routinely used in ophthalmological disease diagnosis and treatment.

Hand-held imaging system 100, shown in FIG. 1(A), includes a Fourier-domain LCI system 102 (also referred to herein as an "LCI system") in which a reference arm 104 and a detection arm 106 of the LCI system 102 receive illumination from a broadband source 108 such as a superluminescent diode (SLD), available from Superlum of Cork, Ireland, centered at a wavelength of 940 nm, with a bandwidth of approximately 70 nm full width at half maximum (FWHM). LCI system 102 also includes a spectrometer unit 120, as available from Wasatch Photonics of Durham, N.C., with a spectral range of 940±40 nm and a line rate of up to 40 kHz, which includes a detector 122, typically, a linescan camera. Additional optical components include a 2×2 fiber coupler 130, with polarization paddles 132 on the reference 104 and sample 106 ports of the fiber coupler, and a free-space reference arm 134 with a mirror 136 for reflecting light back into the interferometer 134.

A hand-held imaging probe 140 (otherwise referred to herein as a "probe housing") houses sample arm 106 of the interferometer 134, along with optics for video otoscopic imaging. A probe nose-cone 142 is typical of those used in otoscopes, modified to include a focusing lens. White light is delivered from an LED (not shown) in the probe housing 140 to the sample via a fiber bundle (not shown) concentrically arranged at the distal end of the probe nose-cone 142. A TM surface 150 (shown in FIG. 1B) is imaged onto a miniature camera 144 using focusing optics 145 located in a handle 146 of the probe. The optical path corresponding to video imaging (in the visible portion of the electromagnetic spectrum) is separated from the LCI imaging path (in the near-infrared portion of the electromagnetic spectrum) using a dichroic mirror 148.

Figure 1B:
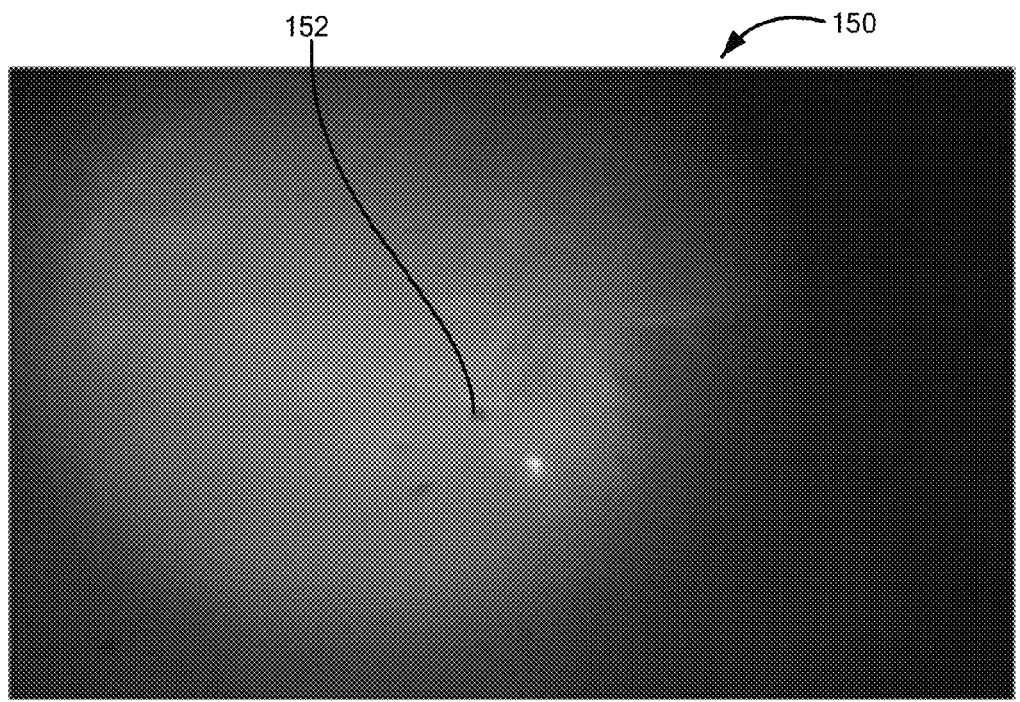
FIG. 1B shows a TM surface image acquired by a CCD camera.
Figure 1C:
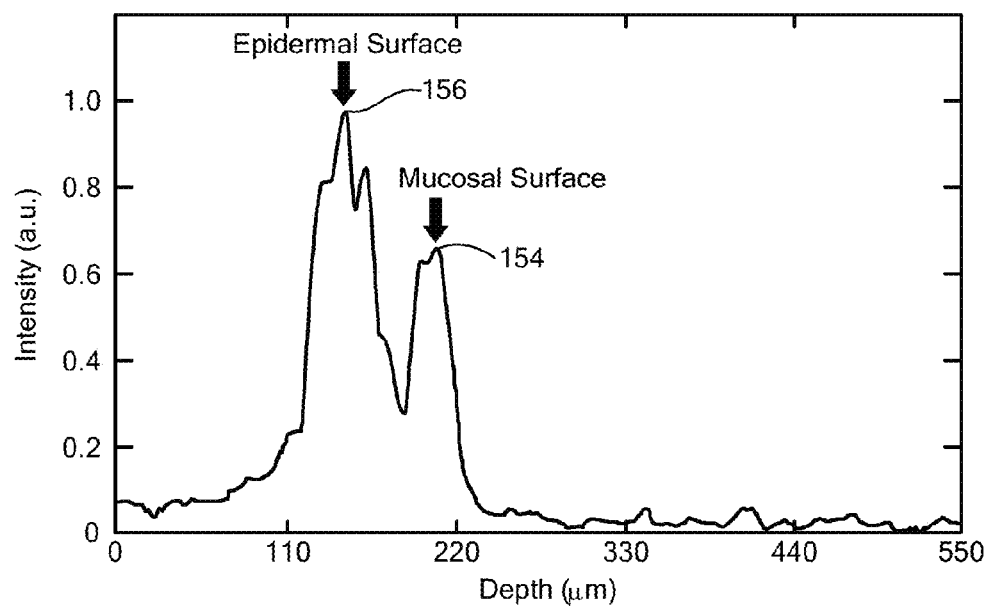
FIG. 1C is an LCI depth scan taken at the point 100 marked in FIG. 1B.

A data-point obtained from the combined LCI-otoscope system 100 comprises a surface image of the TM and corresponding depth-resolved LCI scan data acquired at a fixed point (or "imaging site") 152 in the field-of-view (FOV) of the surface image, as shown in FIGS. 1(B) and (C), respectively. The site 152 on the TM from which the LCI data was obtained is marked by a red asterisk in the surface image shown in FIG. 1B. The TM thickness at the imaging site 152 is obtained by computing the distance between two peaks 154 and 156 in the LCI data, which correspond to the two layers of the TM, namely, the epidermal (outside) and the mucosal (inside) layers.

More specifically, the TM thickness at each imaging site is estimated as the average thickness obtained from a sequence of 100 depth resolved profiles, or A-scans, which were acquired at a rate of 1 kHz. The averaging is performed to provide a more reliable estimate of TM thickness. To obtain the average thickness from a sequence of A-scans, a semi-automated approach is followed in which the multiple 1-D A-scans are first stacked together to build a 2-D M-scan. In the M-scan, the depth information is displayed along the x-axis and the y-axis contains the repeated A-scan measurements. Treating the M-scan as an image, the TM is subsequently segmented by performing an image thresholding operation based on a user-specified threshold level and a region of interest, and the TM thickness is finally obtained as the average thickness of the segmented TM.

To account for the path length change introduced by the refractive index (RI) of the TM, a bulk RI of 1.44 is assumed, following RI measurements reported by Van der Jeught et al., "*Full-field thickness distribution of human tympanic membrane obtained with optical coherence tomography,*" J. Association for Research in Otolaryngology, vol. 14, pp. 483-94 (2013), which is incorporated herein by reference. TM thickness is derived from LCI data. Data are acquired from multiple locations on the TM at a rate of 2 data-points per second (surface image and corresponding LCI data) by manually moving or pointing the hand-held imaging probe over different regions of the TM. On average, 500 data-points are acquired from each TM.

Mosaicking Algorithm

A mosaicking procedure 200, in accordance with a preferred embodiment of the present invention as claimed, is described with reference to FIGS. 2A and 2B. Mosaicking procedure 200 begins with pairwise registration of consecutive pairs of images. As shown in dashed box 202 in FIG. 2B, the pairwise local registration process is performed in three steps. In the first two steps, a coarse feature-based registration of the two images is performed; gross features are extracted 204 and registered 206. For reliable image registration in the presence of imaging artifacts such as nonuniform illumination and blurring, which are inevitably present in images acquired from a hand-held imaging probe, only binary features are used for performing the coarse registration 206. To further mitigate the effect of the aforementioned imaging artifacts, an adaptive thresholding technique, preceded by local histogram equalization for contrast enhancement (taught by Gonzalez et al., "Digital Image Processing Using MATLAB®" (Tata McGraw Hill Education) (2010), and followed by morphological area opening (taught by Soille, "Morphological image analysis: principles and applications" (Springer Science & Business Media) (2013)) to get rid of insignificant spurious features, is used to extract (in step 204) the binary features from the images. The cited references are incorporated herein by reference.

After extracting the binary features from the two images constituting the image pair, coarse registration (206) of the images is performed by assuming a translation-only transformation model. The optimal translation parameters of the model are obtained as the co-ordinates of the maxima of the normalized cross-correlation of the two binary images obtained in the feature extraction step 204. Finally, an intensity-based finer registration 208 of the coarsely registered images is performed. As mentioned earlier, in intensity-based image registration, a similarity metric based on the image pixel values is optimized to estimate the parameters of the transformation matrix.

In accordance with certain embodiments of the present invention, an affine transformation is chosen as the motion model and parameters of the transformation matrix are estimated by optimizing mutual information (MI) between the two images. MI is a metric that measures the dependence between two random variables. In image processing, MI is used as a measure of similarity between two images based on the individual and joint image histograms of the two images. As a measure of image similarity, MI is perhaps one of the most widely used measure for performing image registration because of its several desirable properties such as robustness to the presence of outliers and efficient computation.

For improved convergence, the finer registration 208 is performed only over a region of interest (ROI) that contains significant features. This ROI is identified as the area bounded by the fifth and ninety-fifth percentile of the co-ordinates of the region of overlap between the two coarsely registered binary images obtained from the previous step 206.

Figure 2A:
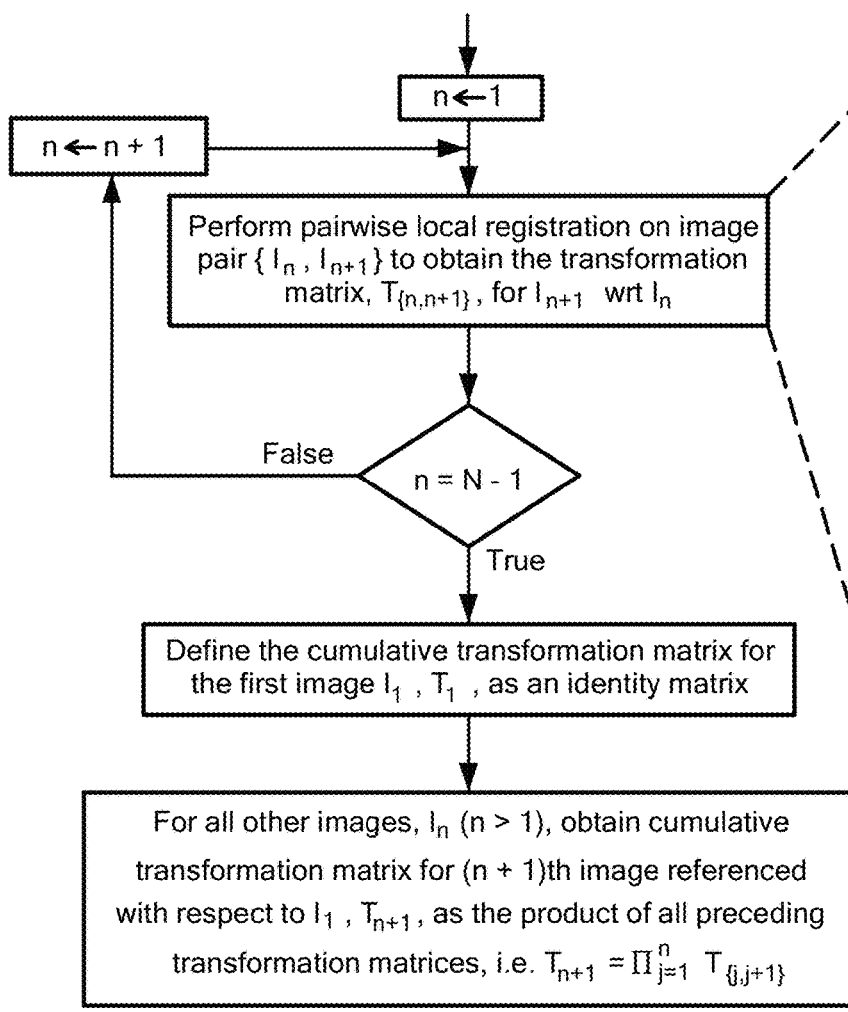
FIGS. 2A and 2B together depict a flowchart of a mosaicking procedure in accordance with an embodiment of the present invention.
Figure 2B:
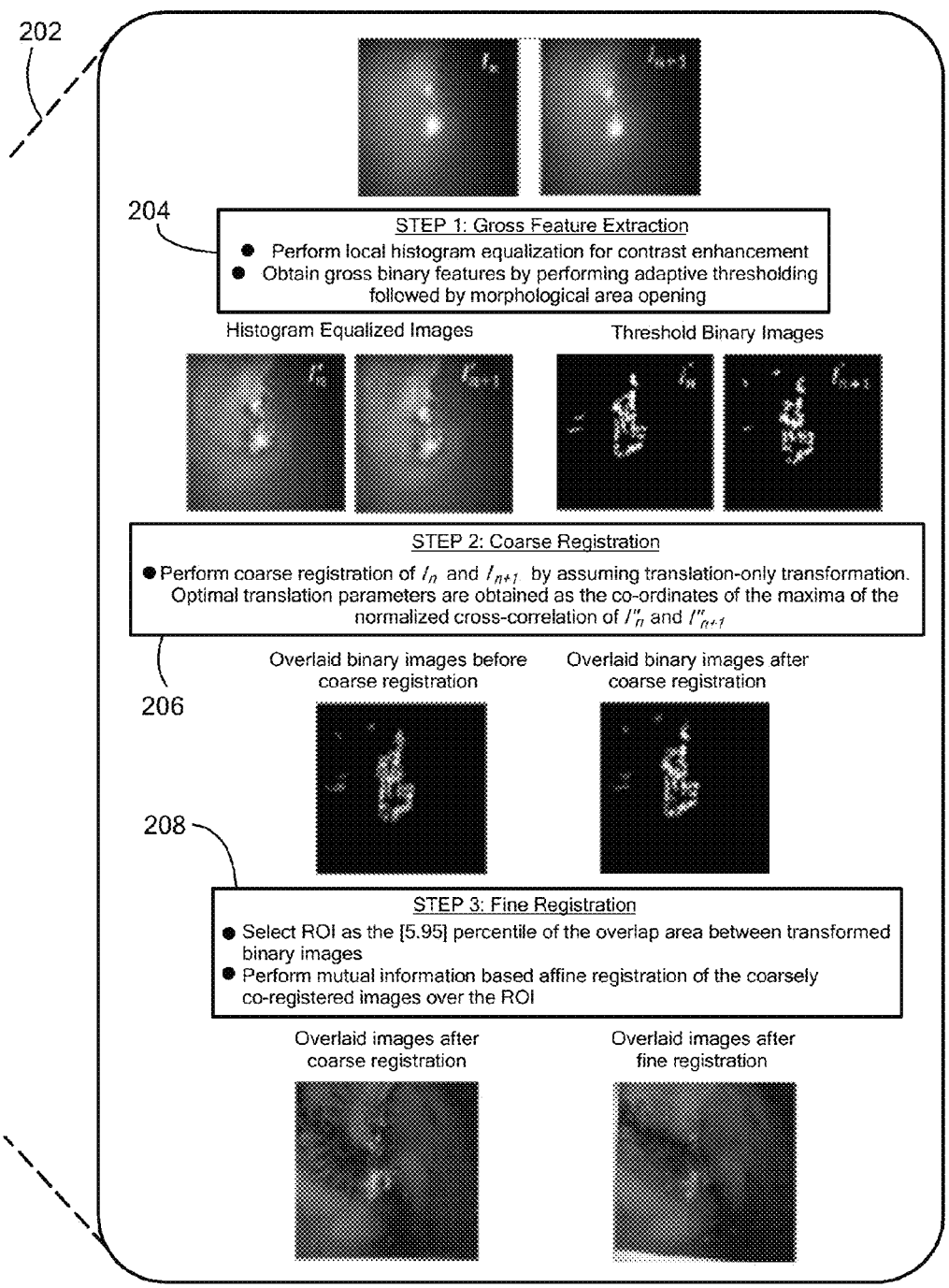

As shown in the flowchart in FIG. 2A, the process of pairwise registration is iteratively performed for all image pairs starting from the first image, which is also assumed to be the reference image. Denoting the transformation matrix characterizing the coordinate transformation between the image pair $\{I_n, I_{n+1}\}$ by $T_{\{n,n+1\}}$, the transformation matrix between a particular image $I_{n+1}$, referenced with respect to the first image, is then obtained by concatenating the preceding pairwise transformation matrices, i.e., $I_{n+1} = \Pi_{j=1}^n T_{\{j,j+1\}}$. The concatenation process provides a means of mapping the individually co-registered images in their local coordinate system to the mosaic coordinate system.

While the aforementioned mosaicking approach works well for a small set of images, in cases where a large number of images have to be co-registered, the concatenation of the pairwise transformation matrices results in an accumulation of errors leading to global alignment errors in the final mosaic. This problem is of greater concern for a sequence of images that loops around, revisiting parts of the imaging scene multiple times at different time points. This is a well-known and well-studied problem in computer vision and various methods to overcome this problem have been reported in the literature.

A solution to the registration closure problem is to divide the sequence of images into smaller sub-sequences of images and to combine the smaller sub-sequences of images into sub-mosaics following the mosaicking procedure described earlier. The same mosaicking process is subsequently applied to the sub-mosaics to obtain the final mosaic.

The final step in generating a mosaic is to blend the individual images constituting the mosaic to get rid of the edges or seams which can occur due to significant differences in brightness and contrast between images. A simple image blending approach is used in accordance with embodiments of the present invention, in which the pixels corresponding to the overlapping regions between a pair of images in the mosaic are assigned the maximum pixel value of the two images.

Since the spatial coordinates of the LCI beam are the same for each surface image, the spatial locations of the points on the TM where the LCI data is acquired may be tracked by using the same co-ordinate transformation matrices that are used to generate the mosaic. Consequently, once all the surface images are registered, the locations corresponding to the LCI imaging sites are readily identified and marked on the full-field mosaic of the TM.

Because the LCI measurements are performed only at a relatively small number (typically about 500) of points on the TM, it is not possible to generate a "true" thickness map for the entire TM. However, treating the thickness measurements at various points on the TM as scattered data, and assuming that the thickness varies smoothly over the entire surface of the TM, scattering data interpolation techniques may be employed to obtain a representative thickness distribution map. One such interpolation algorithm based on penalized least squares regression, has been proposed by Wang et al., "*A three-dimensional gap filling method for large geophysical datasets: Application to global satellite soil moisture observations,*" Environmental Modelling & Software, vol. 30, pp. 139-142 (2012), incorporated herein by reference. The interpolation algorithm of Wang 2012 may be used to generate TM thickness distribution maps in accordance with the present invention.

Examples

In accordance with embodiments of the present invention, LCI system 102 is used to obtain depth-resolved point measurements at several points (hundreds to thousands) on the TM. Using image processing techniques, the depth-resolved point measurements obtained from LCI along with the video data of the surface from which the point measurements are obtained are used to map the imaged points on to an anatomically accurate wide-field surface image of the TM. The thickness values obtained from the LCI data taken at the various points on the TM are subsequently used to obtain an interpolated thickness distribution map of the TM, which is displayed as an overlay on top of the mosaicked full-field image of the TM.

Techniques in accordance with the present invention may advantageously allow 2-D thickness maps (3-D volumes) over a wide imaging field by combining LCI and video imaging in a handheld imaging device. While the present invention has been described herein in terms of mapping the thickness of the TM, it may similarly be used to obtain maps of various structural and functional properties of various tissues and organs, and non-biological materials, all within the scope of the invention.

Figures 3A, 3B, 3C:
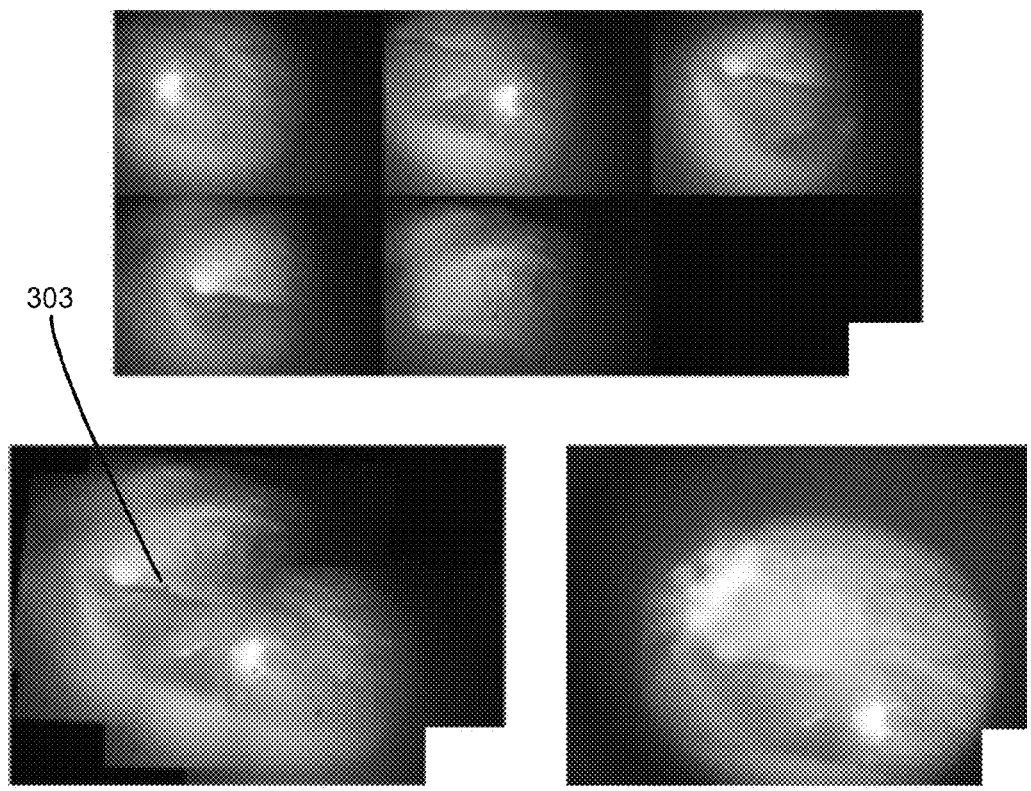
Figure 3D:
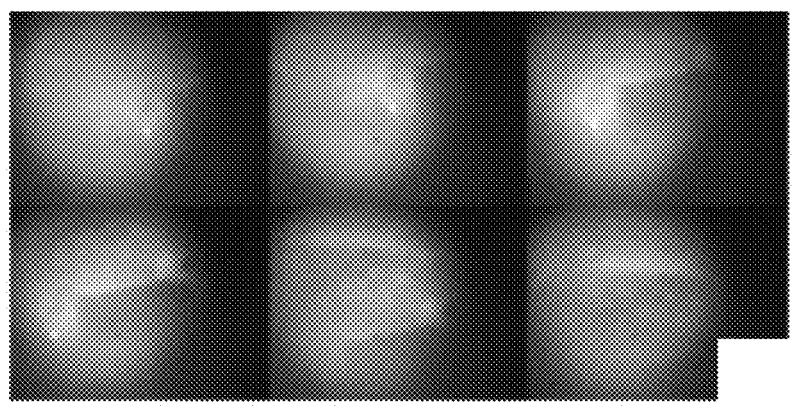
Figure 3D:
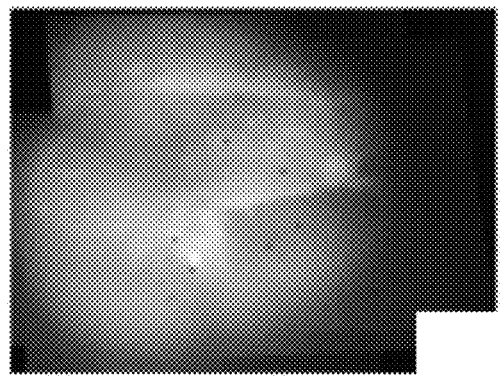
Figure 3D:
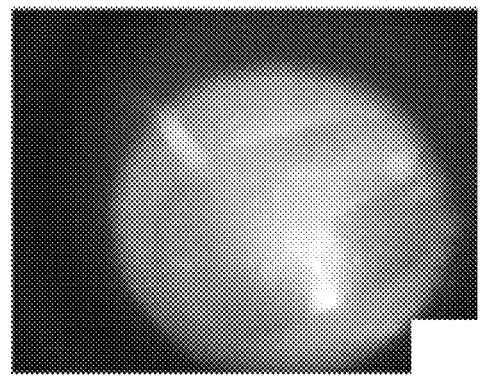
Figure 4A:
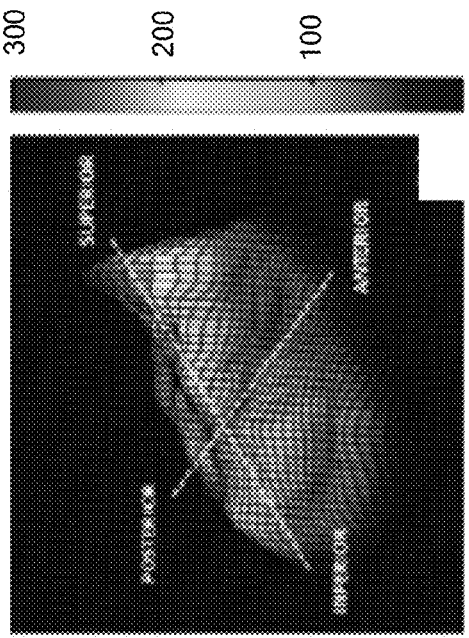
FIG. 4A shows the mosaicked image of a TM. A video-otoscope image of the TM is shown in FIG. 4C.
Figure 4B:
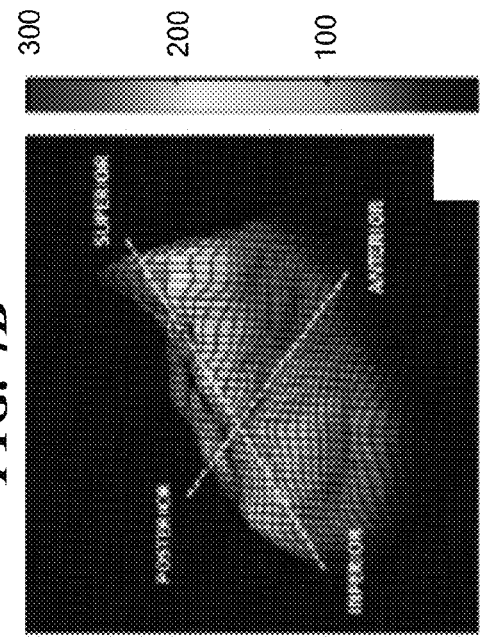
FIGS. 4B and 4D show the thickness distribution map and the overlay image of the thickness distribution map and the mosaic image, respectively.
Figure 4C:
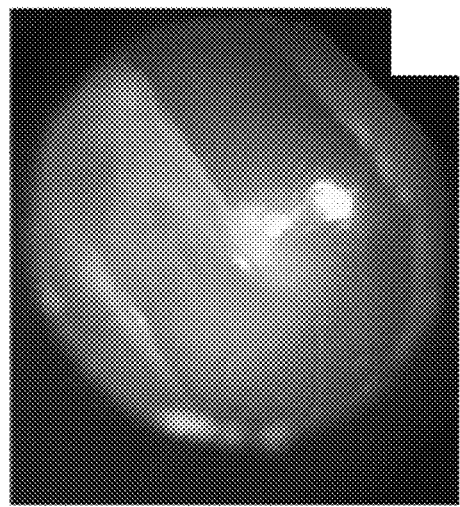
Figure 4D:
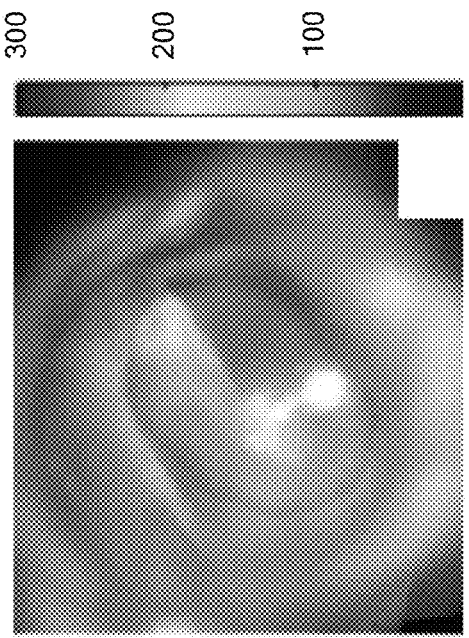

The algorithm described herein was validated on a smaller sequence of two in vivo TM images acquired from two subjects. The validation results from the two subjects are displayed in FIGS. 3A-3C and 3D-3F, respectively. Panels 3A and 3D show the sequence of the small FOV images covering different regions of the TM. Mosaics 301 generated from these images by using the technique described in accordance with the present invention are shown in FIGS. 3B and 3E. Red markers 301 on the mosaicked images correspond to locations of the LCI beam as the imaging probe was moved across the TM surface to image different locations on the TM. For comparison, TM images acquired using a commercial video-otoscope (Welch Allyn Digital MacroView) are displayed in panels 3C and 3F.

Results obtained from a TM sample are presented in FIGS. 4A-4D. Panel 4A shows the mosaicked image of the TM. The video-otoscope image of the TM is shown in panel 4C. Panels 4B and 4D show the thickness distribution map and the overlay image of the thickness distribution map and the mosaic image, respectively. The thickness distribution map shows a region of relatively large thickness starting at the umbo, and extending along the manubrium to include the pars flaccida and the posterior fold at the superior end of the TM. This thicker region is surrounded by a thinner pars tensa region of the TM. Moreover, an increase in thickness around the annular ring surrounding the pars tensa region is also visible in the surface plots of the thickness distribution maps shown in FIG. 4B. These general thickness distribution trends agree with the trends expected in a healthy TM.

Figures 5A, 5B, 5C:
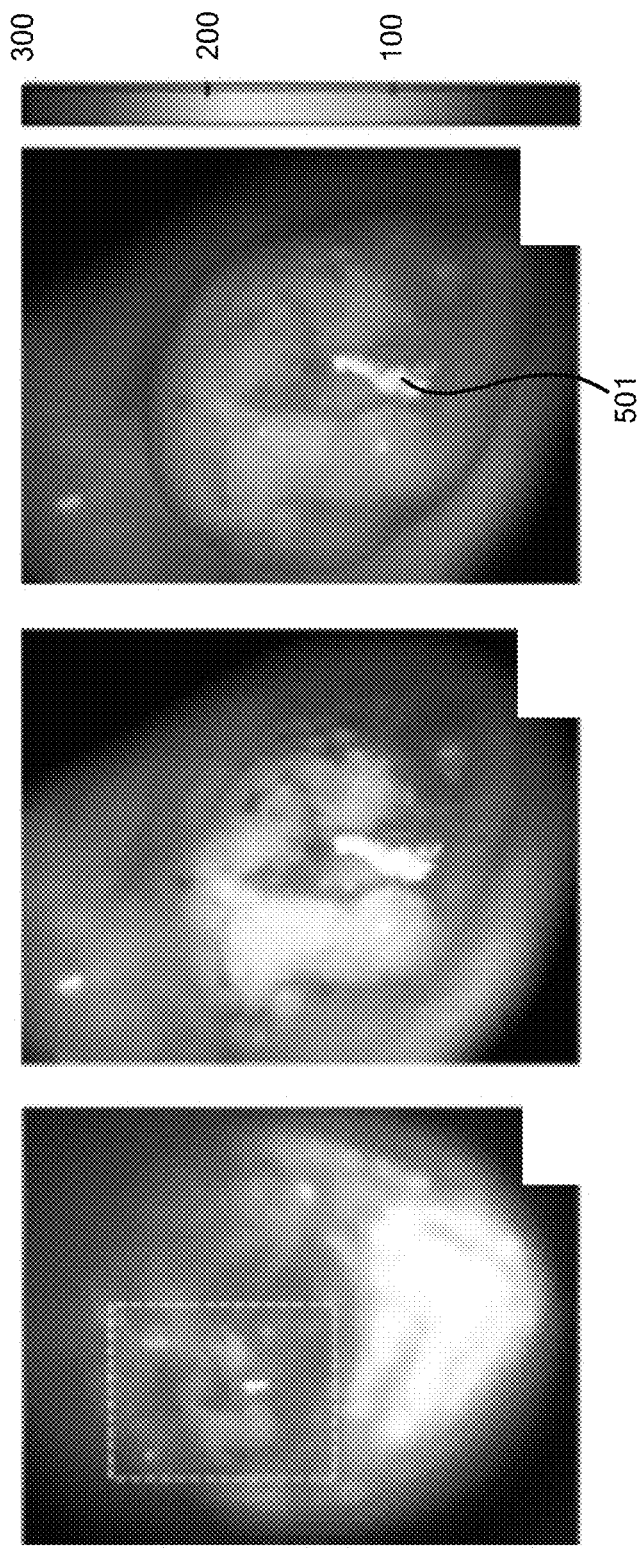
FIG. 5A, shows a video-otoscope image of a TM with a white chalky patch with irregular boundaries typical of tympanosclerosis.
FIG. 5B shows a mosaic obtained from images acquired over the region of interest shown by the orange dashed box in FIG. 5A, in accordance with an embodiment of the present invention. The corresponding thickness distribution map overlaid on top of the mosaic is shown in FIG. 5C.

To demonstrate application in clinical diagnosis of techniques described in accordance with the present invention, the TM of a subject with tympanosclerosis was imaged. The video-otoscope image of that TM, shown in FIG. 5A, shows a region of a white chalky patch with irregular boundaries, a typical presentation of tympanosclerosis. FIG. 5B shows a mosaic obtained from images acquired over the region of interest shown by the orange dashed box in FIG. 5A, and the corresponding thickness distribution map overlaid on top of the mosaic is shown in FIG. 5C. The overlay image clearly shows that the white chalky, scarred region of the TM, which covers a significant part of the pars tensa region, has a thickness much higher than the thickness values typically expected for the pars tensa in a healthy TM.

The quantitative thickness measurements are reported in Table 1 for different anatomical regions of the TM in four studied cases. The different regions, namely the pars flaccida and the four quadrants of the pars tensa, were manually identified and the thickness statistics for each region were computed from the measurements obtained from the imaged sites in the corresponding regions. Moreover, to ensure that only sites from the pars flaccida and pars tensa were used in the analysis, the region around the umbo, the handle of the malleus, and the anterior and posterior folds were excluded while selecting the various regions of the TM.

As expected, the pars flaccida was found to be significantly thicker than the pars tensa region of the TM. The ratio of the mean thickness of pars flaccida to the mean thickness of pars tensa region was computed to be 2.2 for TM1, 2.0 for TM2, 2.2 for TM3 and 1.7 for TM4. The mean and pooled standard deviation of the thickness of the pars tensa for all TM samples was found to be 85.6±33.6 µm. The mean and pooled standard deviation of thickness of the different regions of the TM, computed over all TMs, were found to be 137.7±56.1 µm for the posterosuperior quadrant, 93.4±23.9 µm for the posteroinferior quadrant, 76.4±20.5 µm for the anterosuperior quadrant, and 79.2±20.0 µm for the anteroinferior quadrant. Amongst the different quadrants of the pars tensa, the overall mean thickness of the posterosuperior quadrant was found to be higher than the other quadrants. Likewise, the anterosuperior quadrant had the lowest overall mean thickness. The mean thicknesses of the quadrant-pairs of the four regions of the pars tensa, namely, anterior, posterior, superior, and inferior, were compared for each TM sample by means of an unpaired two-sided unequal variances t-test.

TABLE 1

Descriptive statistics of thickness measurements of TM1-TM4, grouped by different regions of the TM. N, number of measurement sites; other numbers are thickness measurements, with units of microns

| Sample | N | Min | Max | Mean | SD |
|---|---|---|---|---|---|
| Pars Flaccida | | | | | |
| TM1 | 19 | 113.9 | 236.6 | 191.5 | 35.0 |
| TM2 | 26 | 100.0 | 339.1 | 175.0 | 75.6 |
| TM3 | 12 | 104.0 | 332.4 | 170.0 | 60.6 |
| TM4 | 28 | 115.8 | 206.9 | 163.4 | 23.4 |
| Posterosuperior | | | | | |
| TM1 | 11 | 76.1 | 257.2 | 152.7 | 60.1 |
| TM2 | 32 | 73.6 | 168.9 | 104.7 | 24.0 |
| TM3 | 15 | 73.5 | 370.0 | 200.8 | 93.4 |
| TM4 | 17 | 89.5 | 248.2 | 134.4 | 54.3 |
| Posteroinferior | | | | | |
| TM1 | 41 | 62.1 | 162.9 | 105.9 | 20.7 |
| TM2 | 6 | 81.0 | 136.0 | 115.5 | 20.0 |
| TM3 | 57 | 57.7 | 175.9 | 79.8 | 18.3 |
| TM4 | 21 | 75.4 | 208.5 | 99.7 | 39.6 |
| Anterosuperior | | | | | |
| TM1 | 97 | 47.5 | 195.5 | 74.8 | 23.1 |
| TM2 | 46 | 50.6 | 91.6 | 70.2 | 8.9 |
| TM3 | 42 | 40.0 | 80.1 | 58.0 | 10.2 |
| TM4 | 95 | 50.0 | 205.5 | 89.3 | 24.5 |
| Anteroinferior | | | | | |
| TM1 | 162 | 33.3 | 147.1 | 82.6 | 26.0 |
| TM2 | 14 | 68.8 | 150.0 | 93.7 | 24.5 |
| TM3 | 138 | 42.5 | 92.2 | 66.4 | 9.5 |
| TM4 | 50 | 60.4 | 130.2 | 99.4 | 17.5 |
| Complete Pars Tensa | | | | | |
| TM1 | 311 | 33.3 | 257.2 | 85.7 | 30.7 |
| TM2 | 98 | 50.6 | 168.9 | 87.6 | 24.8 |
| TM3 | 252 | 40.0 | 370.0 | 76.0 | 40.8 |
| TM4 | 183 | 50.0 | 248.2 | 97.4 | 31.4 |

It may be noted that, while estimating the thickness of the TM from LCI data, it was assumed that the imaging beam was normally incident on the TM. In practice, the angle between the imaging beam and the TM depends on a multitude of factors. While some of these factors, such as the angle of the TM with respect to the external ear canal, can be quantitatively accounted for based on the average values reported in the literature, other factors, such as the geometry of the ear canal, and the angle of the probe with respect to the TM, which depend on both the subject being imaged and the imaging conditions (probe orientation etc.) are difficult to quantify reliably. The assumption of normal incidence, therefore, provides a potential source of error in our thickness estimates. More specifically, if the TM has an angular tilt of $\theta$ along the axis perpendicular to the imaging beam, then the thickness of the TM based on LCI data is overestimated by a factor of $1/\cos\theta$. To mitigate the angle-related error in thickness measurements, a lateral scanning scheme may be incorporated, within the scope of the present invention, within hand-held probe 140 to obtain B-scans of the TM. The 2-D cross-sectional depth-resolved scans of the TM may then be used to reliably obtain thickness measurements, even in the case when the TM is not exactly perpendicular to the imaging beam, using techniques described by Hubler et al., "*Real-time automated thickness measurement of the in vivo human tympanic membrane using optical coherence tomography,*" Quantitative Imaging in Medicine and Surgery, vol. 5, pp. 69-77 (2015), which is incorporated herein by reference.

Other methods of correcting for geometric and refractive may also be employed within the scope of the present invention, such as those, for example, based upon ray-tracing methods, as discussed, for example, by Westphal et al., "*Correction of geometric and refractive image distortions in optical coherence tomography applying Fermat's principle,*" Opt. Exp., vol. 10, pp. 397-404 (2002), incorporated herein by reference. Correction methods based on lateral scanning would however impose stringent requirements on stability during data acquisition, and would not be suited to hand-held probe-based in-vivo imaging applications.

Other embodiments of the invention allow for a choice of the sub-mosaics determined by computing the local minima of the mean-squared registration error, or other criteria. Further variations of the current teachings, including various techniques for image blending such as Laplacian pyramidal blending and gradient domain blending, may also be used, as may other algorithms for global registration such as bundle adjustment, of which various are discussed by Szeliski 2006.

In accordance with certain embodiments of the present invention, aspects of imaging and, particularly, of imaging otoscopy, described herein may be implemented as a computer program product for use with a computer system. Such implementations may include a series of computer instructions fixed either on a tangible medium, which is preferably non-transient and substantially immutable, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The embodiments of the invention described above are intended to be merely exemplary; numerous variations and modifications will be apparent to those skilled in the art. All such variations and modifications are intended to be within the scope of the present invention as defined in any appended claims.

We claim:

1. A method for acquiring a three-dimensional mapping of a physical specimen characterized by a surface and a refractive index, the method comprising:
   a. obtaining a plurality of surface sub-images of a field of view of the surface of the physical specimen;
   b. obtaining a depth-resolved profile of the physical specimen at one or more fixed locations on each of the plurality of surface sub-images;
   c. extracting at least one of an image feature for use as a landmark for local registration of adjacent sub-images;
   d. pairwise locally registering sub-images to define a set of transformation matrices, each transformation matrix characterizing a coordinate transformation between neighboring sub-images;
   e. iteratively concatenating the transformation matrices so as to reference all of the transformation matrices to one of a plurality of coordinate frames of a plurality of sub-mosaics;
   f. repeating the process of steps (d)-(e) so as to reference all of the transformation matrices to a unitary global coordinate frame of the field of view of the surface of the physical specimen; and
   g. generating a three-dimensional globally co-registered mapping of the physical specimen based in part upon the depth-resolved profile at each of the plurality of locations.

2. A method in accordance with claim 1, further comprising correcting for error due to accumulation of mismatch errors in global registration of sub-mosaics.

3. A method in accordance with claim 1, further comprising interpolating sparsely-sampled areas in such a manner as to generate a smoothly colored map.

4. A method in accordance with claim 1, wherein performing at least one depth scan at the specified point on the surface sub-image includes obtaining and processing a plurality of depth scans at the specified point.

5. A method in accordance with claim 1, further comprising blending edges between neighboring sub-images.

6. A method in accordance with claim 1, further comprising interpolating between depths associated with successive spatial positions.

7. A method in accordance with claim 1, further comprising a step of accounting for increased optical depth due to the refractive index of the physical specimen.

8. A method in accordance with claim 1, wherein the at least one depth scan is obtained using low-coherence interferometry.

9. A method in accordance with claim 1, wherein the physical specimen is a tympanic membrane of a subject.

10. A method in accordance with claim 9, further comprising deriving a measure of the tympanic membrane or of a biofilm disposed thereupon.

11. A three-dimensional otoscopic mapping system comprising:
   a. a hand-held probe having an otoscopic tip for insertion into an ear canal;
   b. focusing optics for directing low-coherence light to ear tissue via the ear canal and for collecting scattered light within a field-of-view of a sub-image of the ear tissue;
   c. a dichroic beamsplitter for reflecting light scattered by a tympanic membrane of a subject onto a camera;
   d. a low-coherence interferometer system for analyzing a depth profile at a plurality of points on the tympanic membrane; and
   e. a processor for mosaicking a plurality of the sub-images and the depth profile at each of the plurality of sub-images to form a map combining two-dimensional surface data with depth data in a visual representation.

12. A three-dimensional otoscopic mapping system in accordance with claim 11, wherein the camera includes a detector array.

13. A three-dimensional otoscopic mapping system in accordance with claim 11, further comprising a steering mirror for scanning the field-of-view of the sub-image across the tympanic membrane.

* * * * *